United States Patent
Qian et al.

(10) Patent No.: US 11,857,274 B2
(45) Date of Patent: Jan. 2, 2024

(54) MEDICAL INSTRUMENT WITH FIDUCIAL MARKERS

(71) Applicant: MediVis, Inc., New York, NY (US)

(72) Inventors: Long Qian, Brooklyn, NY (US); Christopher Morley, New York, NY (US); Osamah Choudhry, New York, NY (US)

(73) Assignee: Medivis, Inc., New York, NY (US)

( * ) Notice: Subject to any disclaimer, the term of this patent is extended or adjusted under 35 U.S.C. 154(b) by 0 days.

(21) Appl. No.: 17/395,233

(22) Filed: Aug. 5, 2021

(65) Prior Publication Data
US 2022/0218419 A1    Jul. 14, 2022

Related U.S. Application Data

(63) Continuation-in-part of application No. 17/148,522, filed on Jan. 13, 2021, now Pat. No. 11,172,996.

(51) Int. Cl.
*A61B 34/20* (2016.01)
*A61B 34/10* (2016.01)
*G06F 3/01* (2006.01)

(52) U.S. Cl.
CPC .............. *A61B 34/20* (2016.02); *A61B 34/10* (2016.02); *A61B 2034/107* (2016.02); *A61B 2034/2068* (2016.02); *G06F 3/011* (2013.01)

(58) Field of Classification Search
None
See application file for complete search history.

(56) References Cited

U.S. PATENT DOCUMENTS

| | | | |
|---|---|---|---|
| 7,427,272 B2 * | 9/2008 | Richard | A61B 34/20 600/595 |
| 2008/0228064 A1 | 9/2008 | Krueger et al. | |
| 2010/0002921 A1 | 1/2010 | Fenchel et al. | |
| 2014/0171787 A1 * | 6/2014 | Garbey | A61B 5/064 600/424 |
| 2015/0265367 A1 * | 9/2015 | Gruhler | G01D 5/34746 600/424 |
| 2018/0193097 A1 | 7/2018 | Mclachlin et al. | |
| 2018/0253856 A1 | 9/2018 | Price et al. | |
| 2019/0090955 A1 * | 3/2019 | Singh | A61B 17/00 |
| 2020/0005486 A1 | 1/2020 | Sinha et al. | |
| 2020/0352655 A1 | 11/2020 | Freese | |
| 2021/0378756 A1 * | 12/2021 | Calloway | G06T 7/38 |

\* cited by examiner

*Primary Examiner* — Patricia J Park
(74) *Attorney, Agent, or Firm* — Cognition IP, P.C.; Edward Steakley; Rajesh Fotedar

(57) ABSTRACT

Various embodiments of a physical instrument are described herein. The physical instrument includes a main tubular body with a first terminal portion and a second terminal portion. The physical instrument further comprises a code platform proximate to the first terminal portion of the main tubular body. The code platform includes a plurality of different codes. The physical instrument also includes at least one of: (i) a flat tip at the second terminal portion and (ii) a passage internal to the main tubular body and extending from the first terminal portion to the second terminal portion.

14 Claims, 15 Drawing Sheets

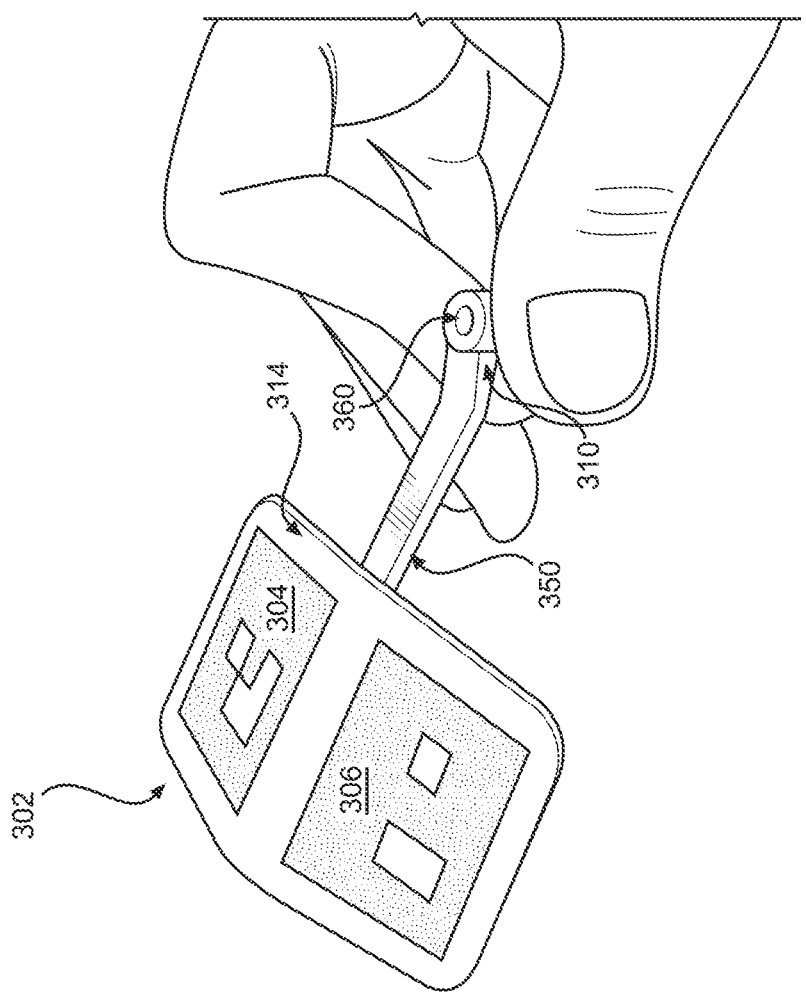

MEDICAL INSTRUMENT WITH FIDUCIAL MARKERS

CROSS REFERENCE TO RELATED APPLICATION

This application is a Continuation-in-Part, and claims the benefit of, U.S. patent application Ser. No. 17/148,522 filed on Jan. 13, 2021, which is incorporated herein by reference in its entirety.

BACKGROUND

Current conventional systems have limitations with regard to two-dimensional (2D) and three-dimensional (3D) images in surgical settings. Surgical planning and surgical navigation are necessary for every medical procedure. A surgeon and their team must have a plan for a case before entering an operating room, not just as a matter of good practice but to minimize malpractice liabilities and to enhance patient outcomes. Surgical planning is often conducted based on medical images including DICOM scans (MRI, CT, etc.), requiring the surgeon to flip through numerous views/slices, and utilizing this information to imagine a 3D model of the patient so that the procedure may be planned. Accordingly, in such a scenario, the best course of action is often a surgeon's judgment call based on the data that they are provided.

SUMMARY

Conventional systems are deficient with respect to tracking fiducial markers disposed on physical instruments. Often, such conventional systems are limited in their ability to generate, render and accurately apply virtual interact ions in an augmented reality environment based on physical orientations and positions resulting from movement and manipulation of physical instruments.

Various embodiments of a physical instrument described herein provide for significant improvements and advantages over such conventional systems. According to one or more embodiments, the physical instrument includes a main tubular body with a first terminal portion and a second terminal portion. It is understood that various embodiments may have multiple terminal portions, such as more than two terminal portions. The physical instrument further comprises a code platform proximate to the first terminal portion of the main tubular body. The code platform includes a plurality of different codes. The physical instrument also includes at least one of: (i) a flat tip at the second terminal portion and (ii) a passage internal to the main tubular body and extending from the first terminal portion to the second terminal portion. It is understood that, in some embodiments, a physical instrument may be a medical surgical instrument. It is further understood that, instead of a flat tip, some embodiments may have a tip that is of a rounded shape, such as a half-sphere.

One or more fiducial markers (or codes) disposed on the code platform may be composed of a non-reflective material that absorbs light (i.e. visible light). According to various embodiments, the one or more fiducial markers may be composed of a material(s) that provides each fiducial marker with a visual contrast against the visual appearance of at least a portion the of the physical instrument. As such, various embodiments of the physical instrument may be tracked by a visible light camera, thereby alleviating a requirement of utilizing a infrared tracking system typically found in conventional systems.

It is understood that the various embodiments of the physical instrument may be utilized in conjunction with an augmented reality (AR) display system. For example, the AR display system may one or more embodiments of a Registration Engine as described in U.S. patent application Ser. No. 17/148,522 filed on Jan. 13, 2021.

According to various embodiments, the physical instrument may be an anatomical landmark registration localizer (hereinafter "localizer"). The localizer includes a plurality of fiducial markers that can be tracked via an AR display system. According to various embodiments, an end-user wearing an AR display headset may manipulate the localizer by hand while the AR display system integrates a visualization of the localizer within an interactive AR environment displayed and viewed via the AR display headset.

The end-user may place the tip of the localizer at one or more locations of an anatomical region of an individual's physical body, whereby each respective location may be a landmark the end-user desires to be registered by the AR display system. To register a landmark within the anatomical region, the AR display system determines a physical position and orientation of the localizer with respect to a fixed reference position of a three-dimensional (3D) unified coordinate system.

Upon receipt of the indication from the end-user that the flat tip is in contact with a desired landmark, the AR display system captures the coordinates of one or more fiducial markers disposed on the physical instrument. The AR display system further calculates one or more spatial transformations and executes position mapping based on the fiducial marker coordinates in order to calculate coordinates that represent a position of the desired landmarks on the individual's body within the 3D unified coordinate system.

In some embodiments, the physical instrument may be a sheath. A trajectory for a surgical instrument or tool may be planned via the AR display system. For example, the AR display system may generate and render a trajectory line for display by the AR display headset. The trajectory may be based on a target point and an entry point, whereby both the target point and the entry may both correspond to different 3D medical model data concurrently displayed by the AR display system. The target point may correspond to 3D medical model data that represents an internal anatomical region and the entry point may correspond to 3D medical model data for an outer anatomical region, such as a particular location on a skin surface.

The AR display system may generate and render an AR display of the trajectory via the AR display headset. An end-user wearing the AR display headset may manipulate the sheath by hand while the AR display system integrates a visualization of both the rendered trajectory and the sheath within an interactive AR environment displayed and viewed via the AR display headset. The AR display system determines a physical position and orientation of the sheath with respect to a fixed reference position of a three-dimensional (3D) unified coordinate system. The target and entry points for a trajectory are based on coordinates selected with the localizer whereby each of the target and entry point is a difference coordinate in the 3D unified coordinate system.

The AR display system captures coordinates of one or more fiducial markers disposed on the sheath. The AR display system further calculates one or more spatial transformations and executes position mapping based on the fiducial marker coordinates in order to calculate and verify whether a portion of the sheath has a current physical orientation that is in alignment with the respective coordinates that occur along the rendered trajectory. For example, the AR display system may capture coordinates of the one or more fiducial markers to determine whether a physical orientation of a main tubular body of the sheath is aligned with the rendered trajectory. The main tubular body further includes an internal passage through which a physical surgical instrument or tool may be inserted into and through the main tubular body such that the physical surgical instrument or tool exits the main tubular body along the rendered trajectory.

According to various embodiments, the code platform of the physical instrument may include a plurality of codes. Each respective code may be disposed on a top surface of the code platform and be composed of a non-reflective material that absorbs light. For example, the code platform may include a first hamming code and a second hamming code. The first hamming code may be different than the second hamming code. An error tolerance exists between the first and the second hamming codes.

In various embodiments, the first hamming code is situated within a first fiducial marker region of the code platform and the second hamming code is situated within a second fiducial marker region of the code platform.

Further areas of applicability of the present disclosure will become apparent from the detailed description, the claims and the drawings. The detailed description and specific examples are intended for illustration only and are not intended to limit the scope of the disclosure.

BRIEF DESCRIPTION OF THE DRAWINGS

The present disclosure will become better understood from the detailed description and the drawings, wherein:

FIG. 15 is a diagram illustrating a type of perspective view of an exemplary embodiment.

DETAILED DESCRIPTION

Figure 1:
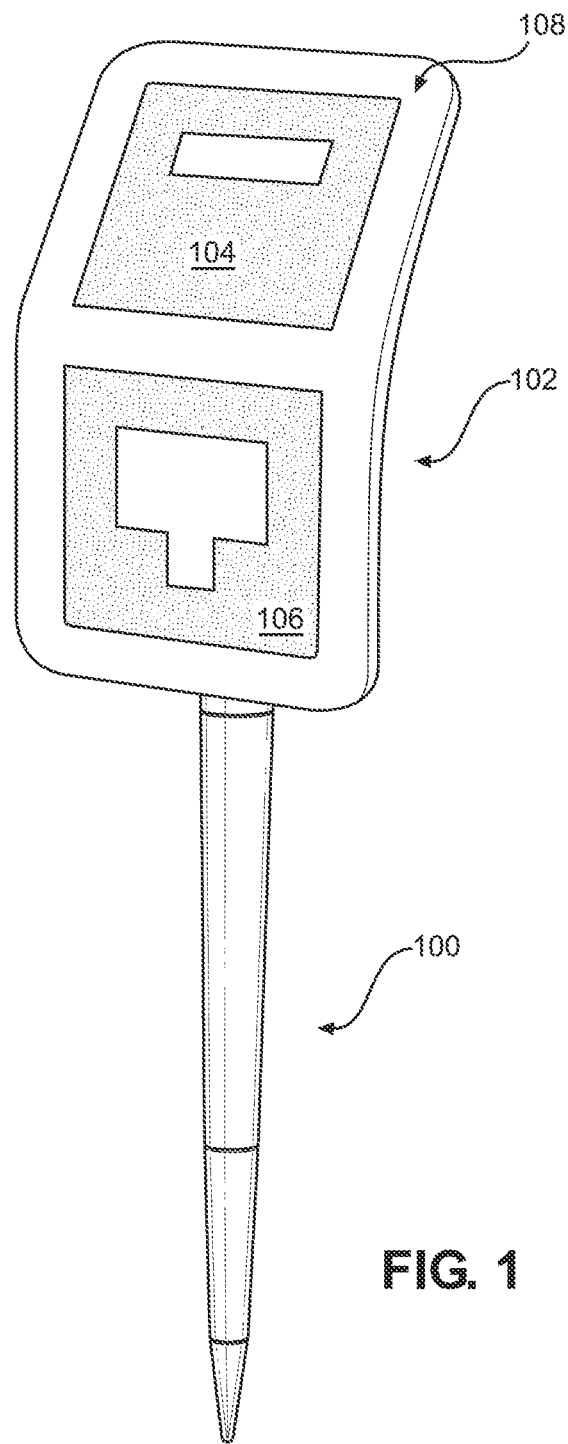
FIG. 1 is a diagram illustrating a type of perspective view of an exemplary embodiment.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

As shown in FIG. 1, an embodiment of a localizer (or a sheath as described herein) may have a main tubular body 100 and a code platform 102. The code platform 102 may include one or more codes 104, 106. In some embodiments, the codes 104, 106 may be different hamming codes. A padding 108 may further be disposed on the code platform 102. For example, the padding 108 may border one or more edges of each of the codes 104, 106 on the code platform 102. The one or more codes 104, 106 may be composed of a non-reflective material that absorbs light. As such, various embodiments of the physical instrument may be tracked by a visible light camera, thereby alleviate the requirement of utilizing an infrared tracking system typically found in conventional systems. In some embodiments, the physical instrument may be composed of a plastic nylon material, stainless steel or aluminum. In some embodiments, the physical instrument may be a medical instrument with a composition that includes a sterilized material, such as a material sterilized via gamma-sterilization or auto-clave.

Figure 2:
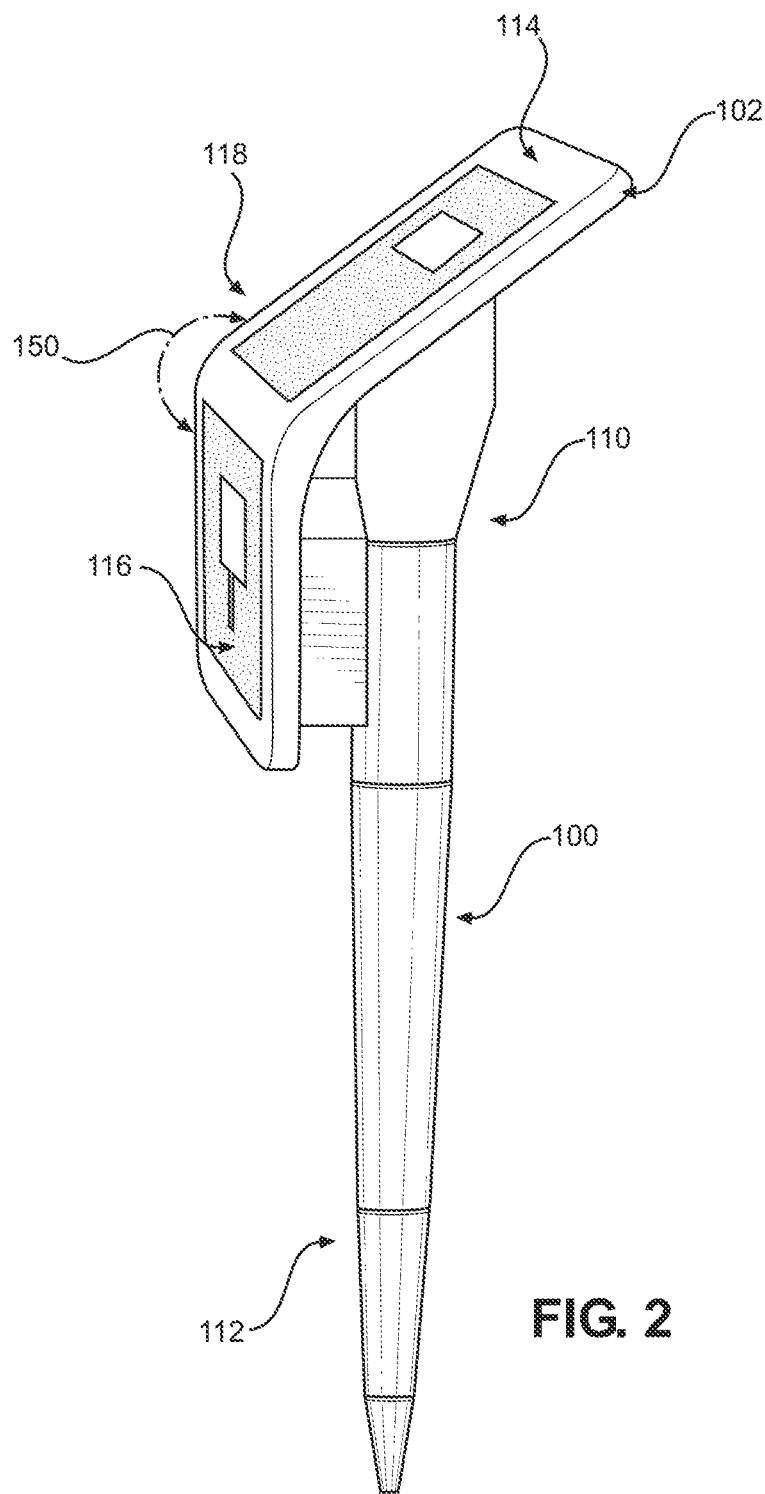
FIG. 2 is a diagram illustrating a type of perspective view of an exemplary embodiment.

As shown in FIG. 2, the code platform 102 may have a top surface 114. The top surface 114 may include a first fiducial marker region 116 and a second fiducial marker region 118. It is understood that, in various embodiments, the first and second fiducial marker regions 116, 118 may be the one or more codes 104, 106—respectively. A portion of the code platform 102 that includes the first fiducial marker region 116 may be disposed on the localizer such that region 116 is parallel to the main tubular body 100. The main tubular body 100 may have a first terminal portion 110 and a second terminal portion 112. The code platform 102 may be connected to the first terminal portion 110. The second fiducial marker region 118 may be angled towards the first terminal portion 110 such that a degree amount 150 that is greater than 180 exists between the respective fiducial marker regions 116, 118. In various embodiments, the tubular body 100 may have one or more measurement markings representing distance from the tip.

Figure 3:
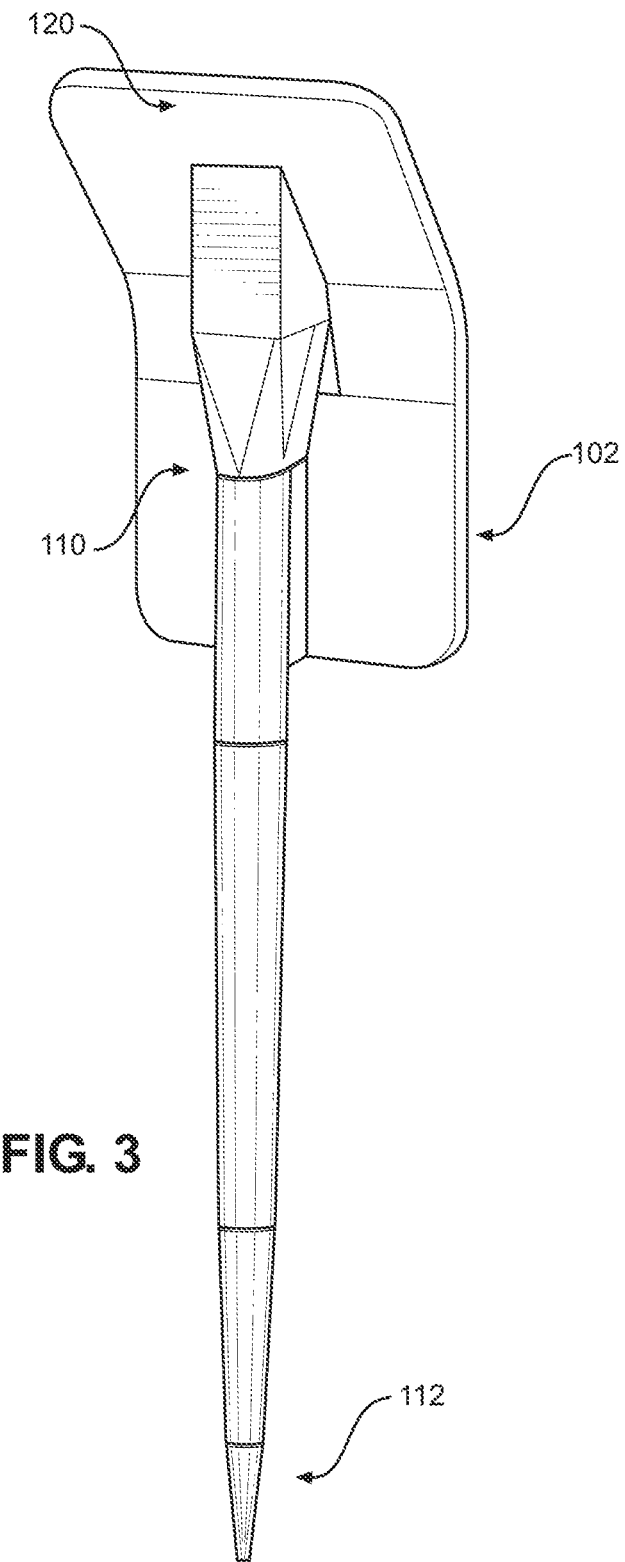
FIG. 3 is a diagram illustrating a type of perspective view of an exemplary embodiment.
Figure 4:
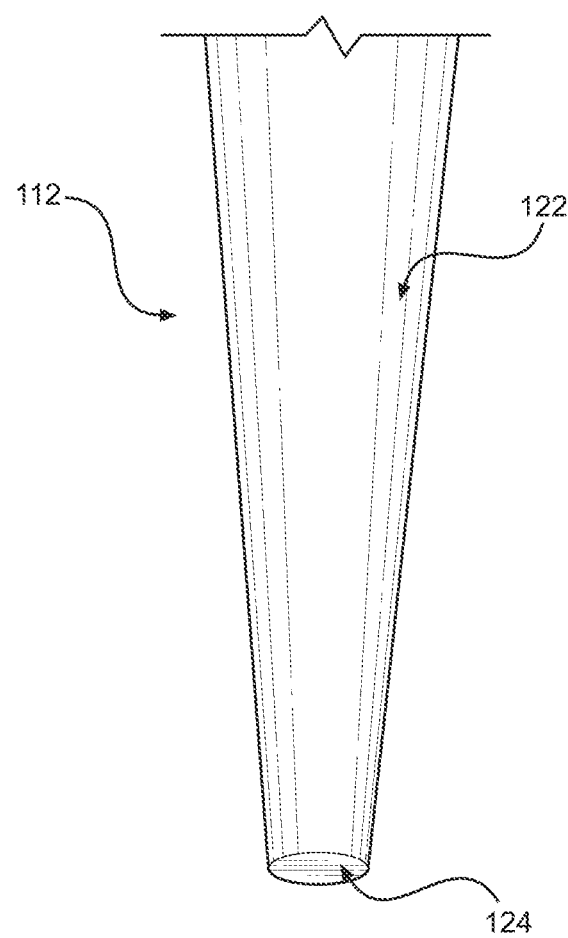
FIG. 4 is a diagram illustrating a type of perspective view of an exemplary embodiment.

As shown in FIG. 3, a bottom surface 120 of the code platform 102 may be connected to the first terminal portion 110. As shown in FIG. 4, the second terminal portion 112 may include a tapered tubular segment 122. The tapered tubular segment 122 may further include a flat tip 124 of the main tubular body 100.

Figure 5:
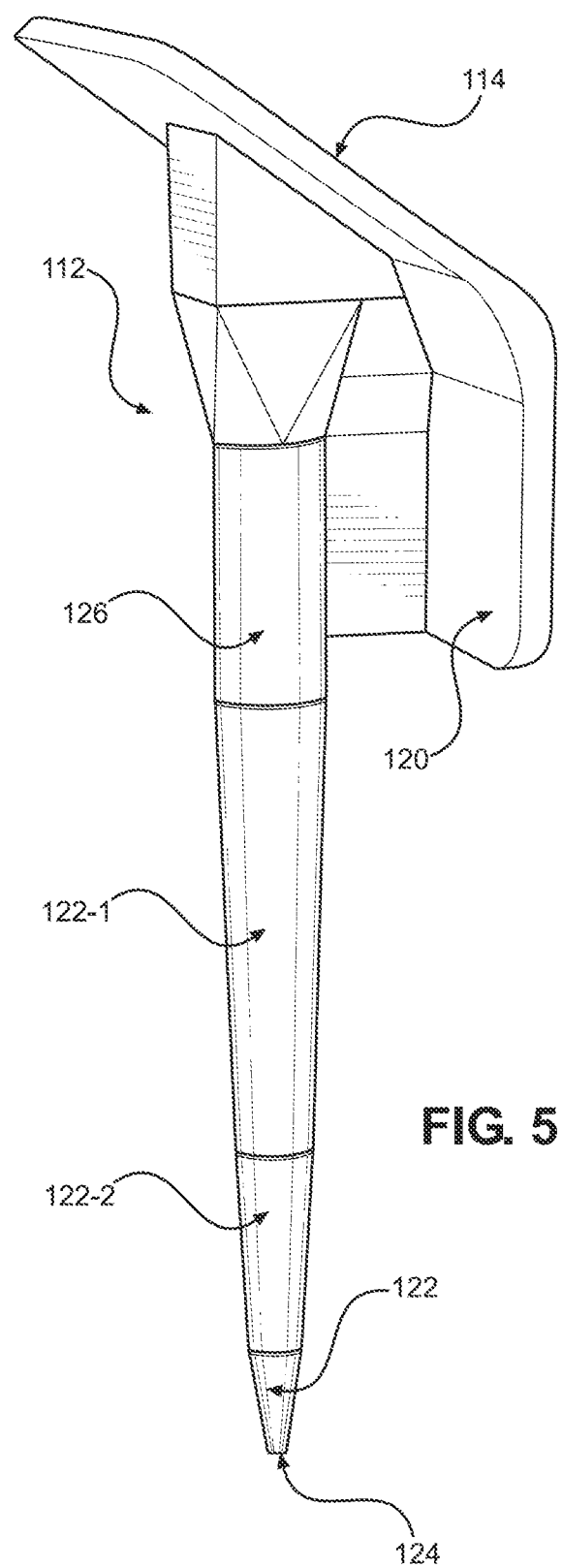
FIG. 5 is a diagram illustrating a type of perspective view of an exemplary embodiment.

As shown in FIG. 5, the main tubular body 100 may include a tubular segment 126 and one or more tapered tubular segments 122, 122-1, 122-2. It is understood that all of the tapered tubular segments 122, 122-1, 122-2 illustrated in FIG. 5 may be interpreted as each being a respective part of a single tapered tubular segment that is adjacent to the tubular segment 126. The tapered tubular segment 122 may have a first segment portion with a first diameter that is larger than a second diameter at a second segment portion, whereby the second diameter is substantially similar to a diameter of the flat tip 124.

Figure 6:
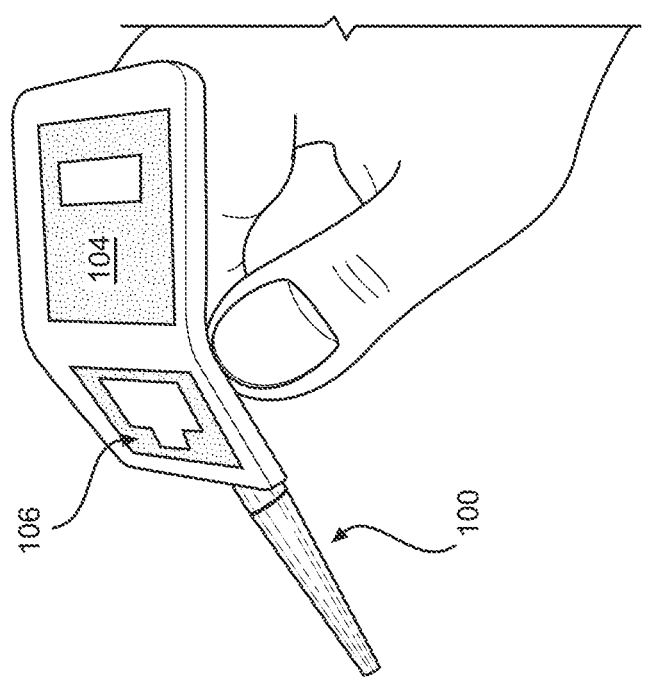
FIG. 6 is a diagram illustrating a type of perspective view of an exemplary embodiment.
Figure 7:
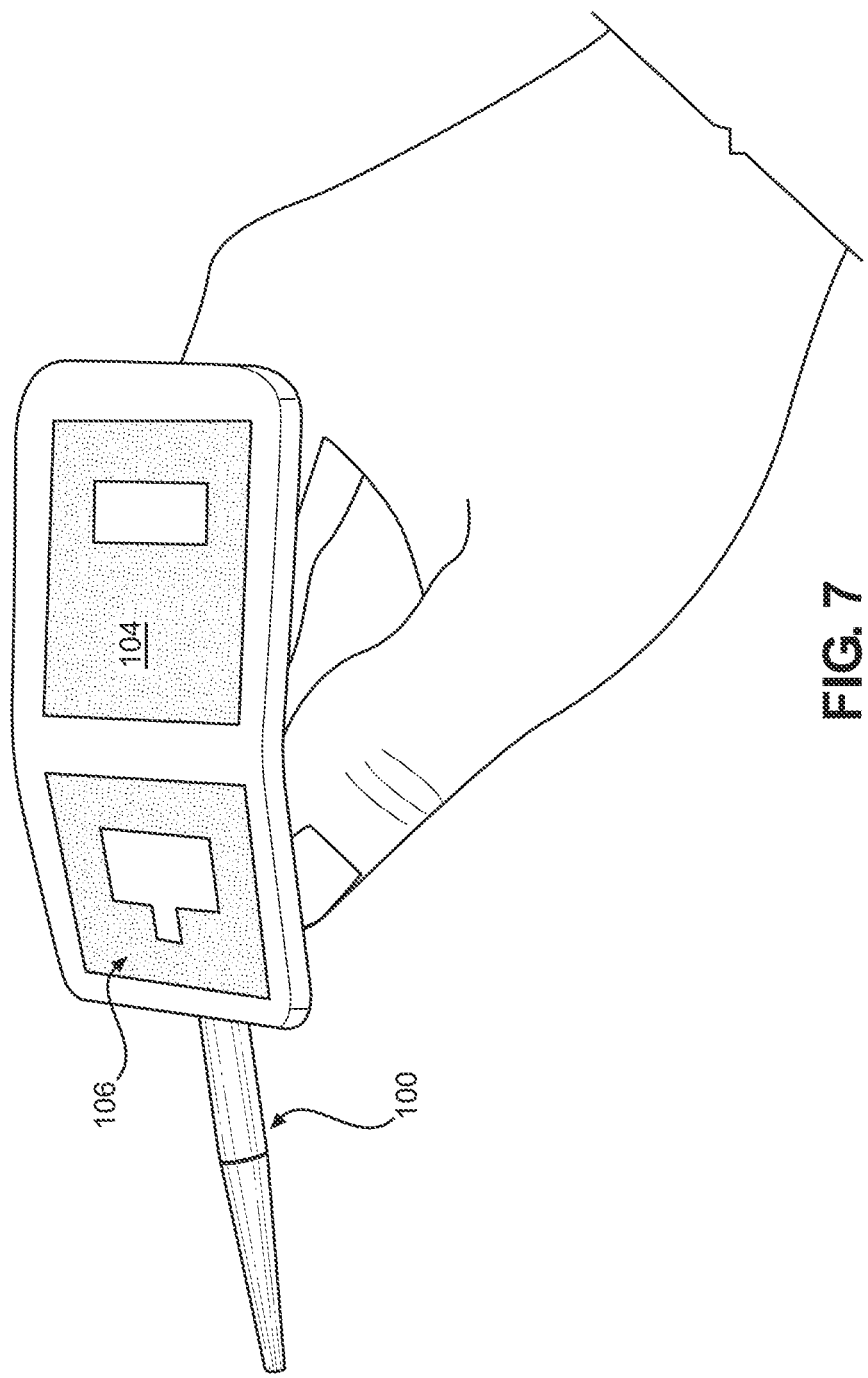
FIG. 7 is a diagram illustrating a type of perspective view of an exemplary embodiment.

FIGS. 6-7 each illustrate a hand position for holding an embodiment of the localizer.

It is understood that while various portions and/or segments of the physical instrument are described herein as having a tubular shape(s). Various embodiments of the physical instrument are not restricted or limited to only having tubular portions and/or tubular segments.

Figure 8:
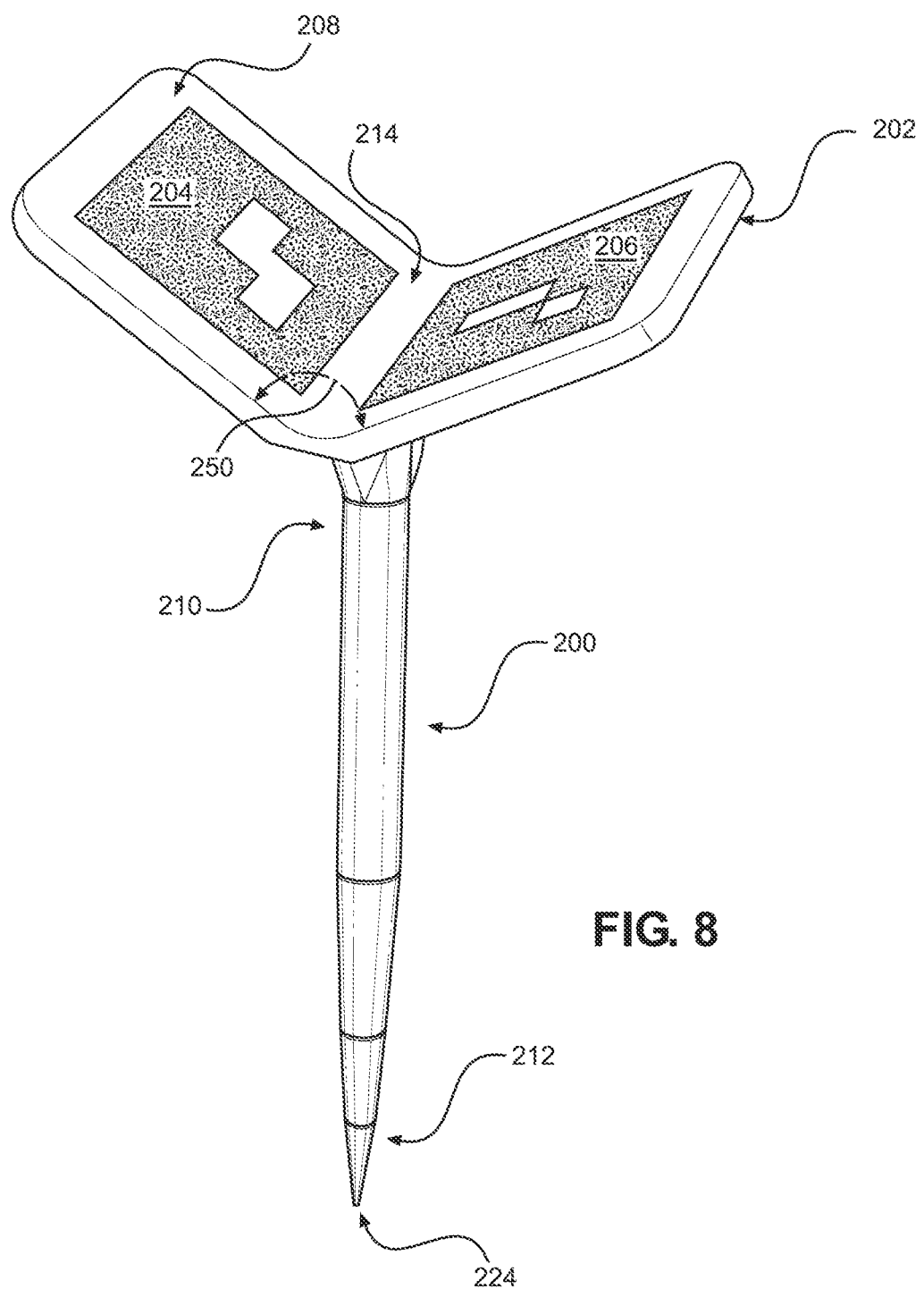
FIG. 8 is a diagram illustrating a type of perspective view of an exemplary embodiment.

As shown in FIG. 8, an embodiment of the localizer may include a main tubular body 200. The main tubular body 200 may have a first terminal portion 210 and a second terminal portion 212. The second terminal portion 212 may and in a flat tip 224. A code platform 202 may be proximate to the first terminal portion 210. The code platform 202 may have a top surface that includes one or more codes 204, 206 and a padding 208 that surrounds and borders the respective edges of the codes 204, 206.

The one or more codes 204, 206 may be angled away from the main tubular body 200. For example, each code 204, 206 may be a respective fiducial marker region disposed on the top surface 214 of the code platform 202. As shown in FIG. 8, wherein the localizer is oriented in a vertical position with the code platform 202 above the flat tip 224, the code platform 202 may be shaped according to a "V" formation such that a central portion of the code platform 202 is attached to the first terminal portion 210 and a degree amount 250 that is less than 180° exists between the fiducial marker regions on the top surface 214. In other embodiments, the degree amount 250 may be larger than 180°, to result in an "upside down V" formation.

Figure 9:
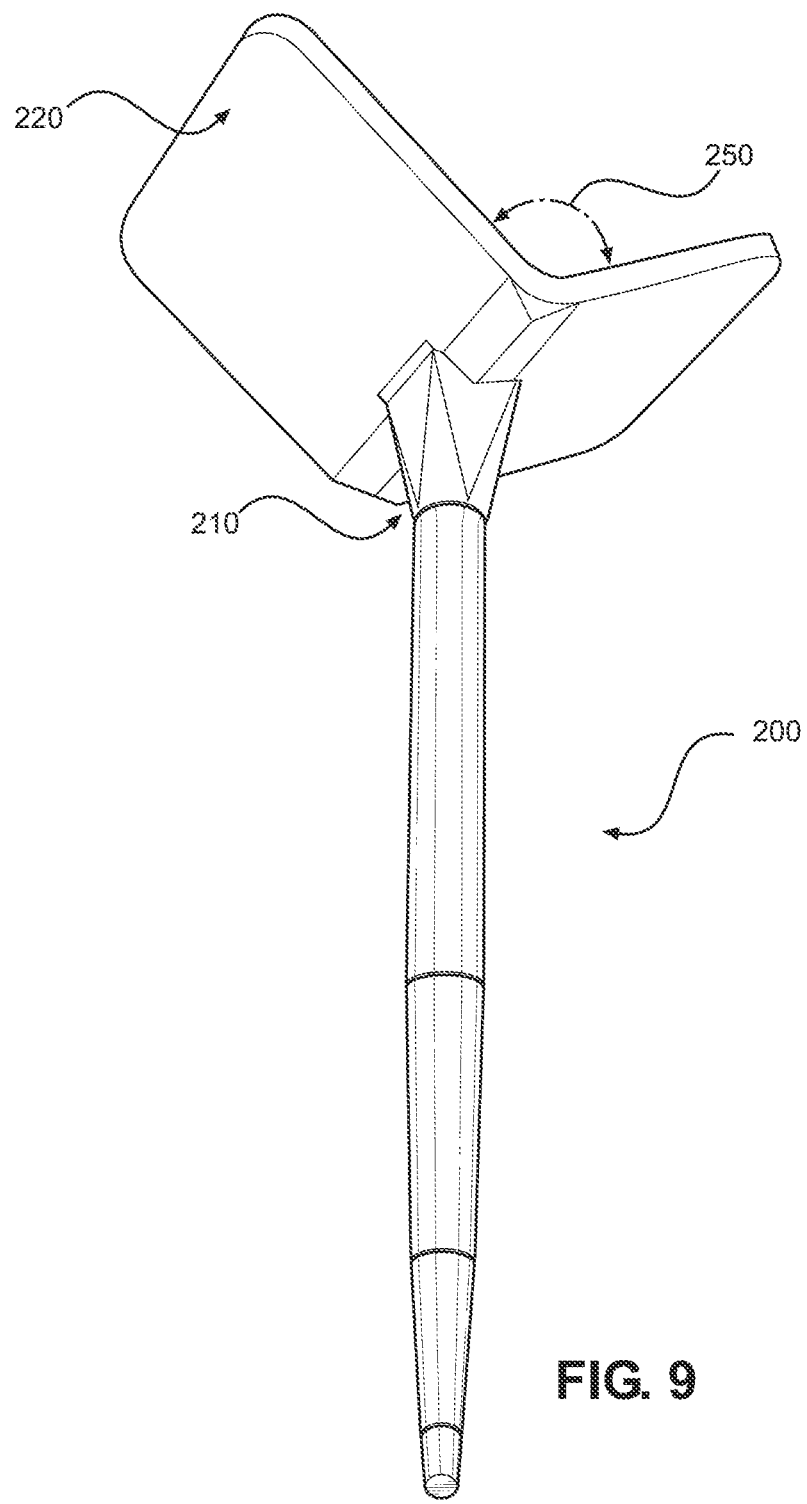
FIG. 9 is a diagram illustrating a type of perspective view of an exemplary embodiment.
Figure 10:
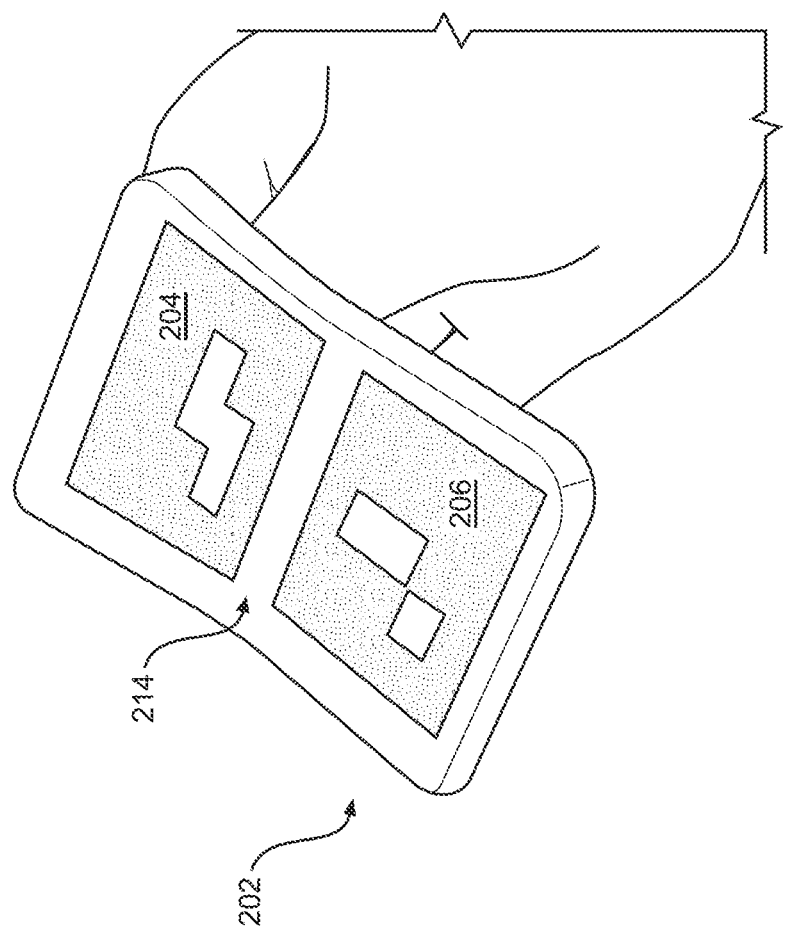
FIG. 10 is a diagram illustrating a type of perspective view of an exemplary embodiment.
Figure 11:
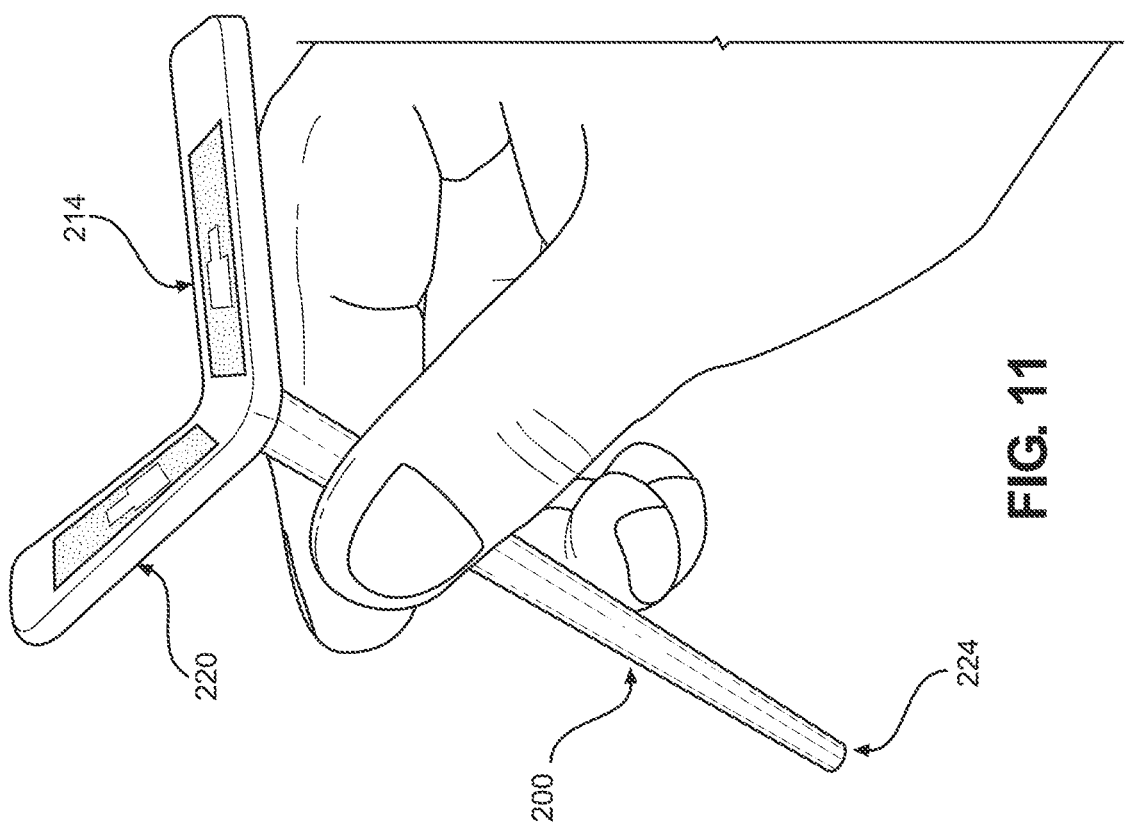
FIG. 11 is a diagram illustrating a type of perspective view of an exemplary embodiment.

As shown in FIG. 9, the code platform 202 may have a bottom surface 220 that is attached to the first terminal portion 210. FIGS. 10-11 each illustrate a hand position for holding an embodiment of the localizer. FIG. 10 provides a perspective view directly above the top surface 214 of the code platform 202 resulting from the hand position for holding the localizer. FIG. 11 provides a perspective side view of the localizer resulting from the hand position for holding the localizer.

Figure 12:
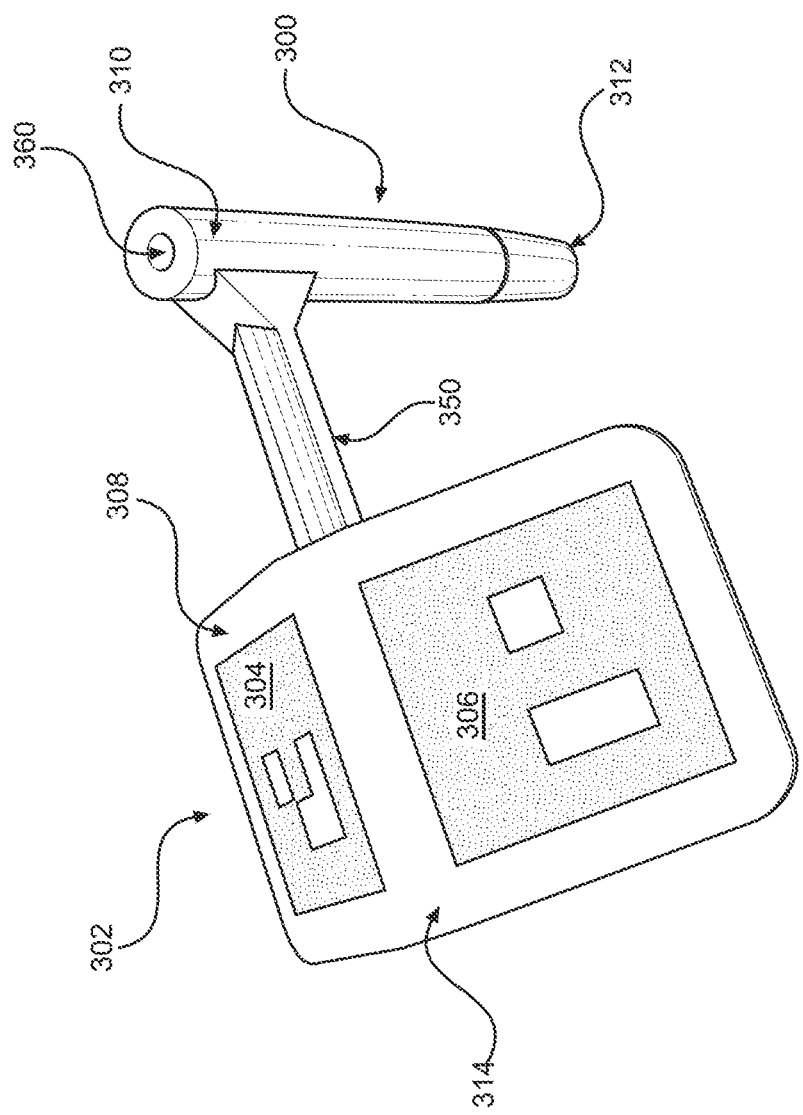
FIG. 12 is a diagram illustrating a type of perspective view of an exemplary embodiment.

As shown in FIG. 12, an embodiment of a sheath may include a main tubular body 300. The main tubular body 300 may include a first terminal portion 310 and a second terminal portion 312. An arm 350 may extend perpendicularly away from the main tubular body 300. The arm 350 may be attached to the main tubular body 300 proximate to the first terminal portion 310. The arm 350 may be connected to a code platform 302. The code platform 302 may have a top surface 314 upon which one or more codes 304, 306 are disposed. The top surface 314 may have a padding 308 that surrounds the respective codes 304, 306 and borders the respective codes 304, 306. The one or more codes 304, 306 may be angled downwards and towards the direction of the second terminal portion 312. The main tubular body 300 may include a first opening of internal passage 360 that extends from an edge of the first terminal portion 310 to an edge of the second terminal portion 312.

Figure 13:
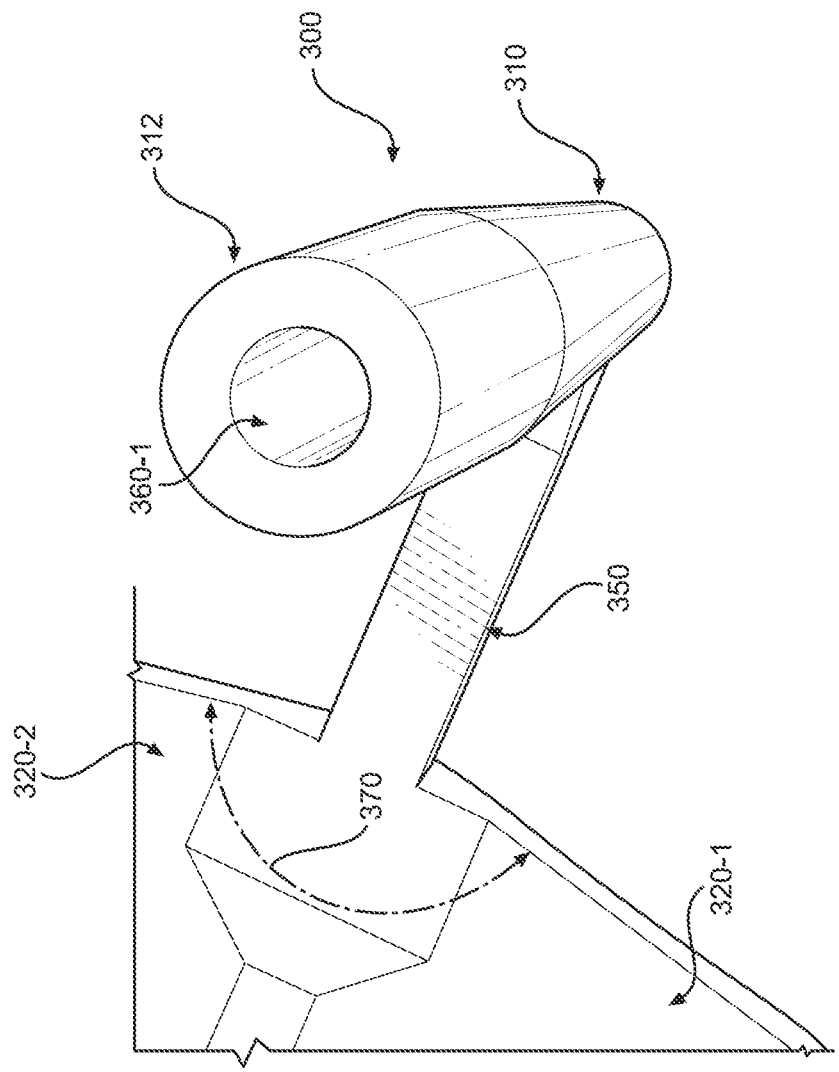
FIG. 13 is a diagram illustrating a type of perspective view of an exemplary embodiment.

As shown in FIG. 13, a second opening of the internal passage 360-1 may be included at the edge of the second terminal portion 312. As the codes 304, 306 on the top surface 314 are angled away from each other, a degree amount 370 less than 180° exists between a first portion of the bottom surface 320 and a second portion of the bottom surface 320. In other embodiments, the degree amount 250 may be larger than 180°, whereby the code platform 302 comprises a "V" formation.

Figure 14:
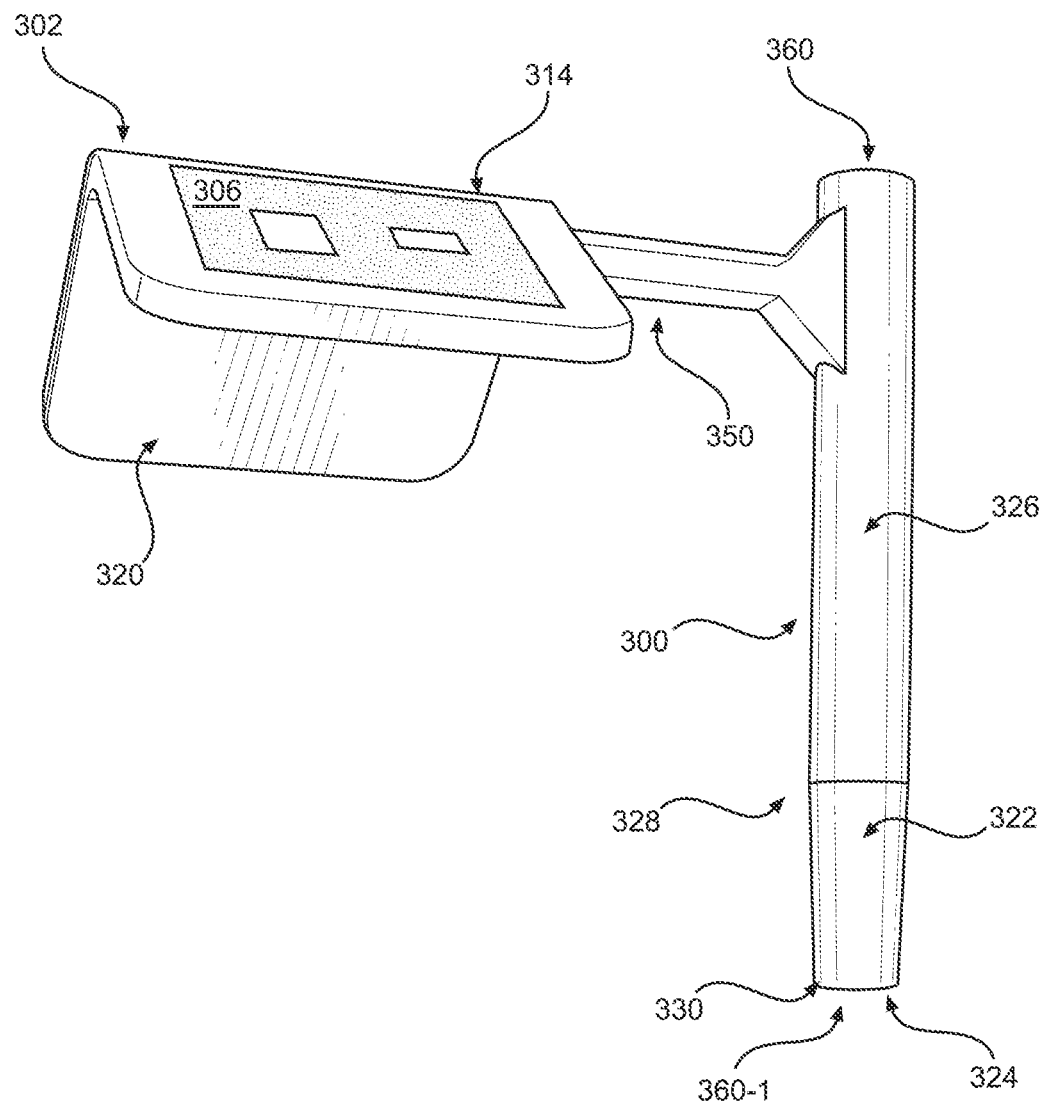
FIG. 14 is a diagram illustrating a type of perspective view of an exemplary embodiment.

As shown in FIG. 14, the arm 350 connects the code platform 302 to the main tubular body 300. An internal passage extends throughout and within the main tubular body 300. The internal passage is accessible via openings 360, 360-1 at terminal portions of the main tubular body 300. The main tubular body 300 further includes a tapered tubular segment 322 and a tubular segment 326. The tapered tubular segment 322 includes the flat tip 324. A first diameter 328 of the tapered tubular segment 322 may be equal to a diameter of a portion of the first tubular segment 326. A second diameter 330 of the tapered tubular segment 322 may be a diameter of the flat tip itself 324. A particular passage opening 360-1 may be accessible at the flat tip 324.

FIG. 15 provides a perspective side view of a hand position for holding the sheath.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A physical instrument comprising:
   a main tubular body with a first terminus and a second terminus;
   a code platform comprising a first and a second code region, a first code disposed on a top surface of the first code region and a second code disposed on a top surface of the second code region;
   a tip at the second terminus;
   a first portion of a bottom surface of the code platform situated below the first code, the first portion of the bottom surface attached to the first terminus of the main tubular body;
   a second portion of the bottom surface of the code platform situated below the second code;
   wherein an angle of less than 180 degrees exists between the first portion of the bottom surface of the code platform and the second portion of the bottom surface of the code platform; and
   wherein a physical orientation of the second code region is parallel to at least a portion of the main tubular body.

2. The physical instrument of claim 1, wherein the first code comprises a first hamming code and wherein the second code comprises a second hamming code, the first hamming code being different than the second hamming code;
   wherein an error tolerance exists between the first and the second hamming codes.

3. The physical instrument of claim 2, wherein the first and the second hamming codes are both composed of a non-reflective material that absorbs light.

4. The physical instrument of claim 1, wherein the code platform comprises a padding bordering the first and the second code regions.

5. The physical instrument of claim 4, wherein a color of the padding differs from a color of the first and the second codes, wherein a difference between the color of the padding and the color of the first and the second codes results in a high degree of visual contrast between the padding the respective codes.

6. The physical instrument of claim 1, comprising: wherein the first code differs from the second code.

7. The physical instrument of claim 1, wherein the main tubular body comprises at least a first part of a tubular segment and a second part of the tapered tubular segment;
   wherein the second part of the tapered tubular segment ("tapered tip") includes the tip; and
   wherein the code platform is more proximate to the first part of the tubular segment than the tapered tip.

8. The physical instrument of claim 1, wherein the tip is one of: a flat tip or a tip have a round half-sphere shape.

9. The physical instrument of claim 1, where in the physical instrument comprises a medical surgical instrument.

10. The physical instrument of claim 1, wherein an edge segment of the code platform extends between the top surface and the bottom surface of the code platform.

11. A physical instrument comprising:
   a main tubular body with a first terminal portion and a second terminal portion;
   a code platform proximate to the first terminal portion of the main tubular body, the code platform including a plurality of different codes;
   a tip at the second terminal portion;
   wherein the physical instrument comprises an anatomical landmark registration localizer; and
      wherein the code platform comprises a first fiducial marker region and a second fiducial marker region disposed on a top surface of the code platform and a bottom surface of the code platform, the bottom surface connected to the first terminal portion of the main tubular body, wherein a first portion of the bottom surface under the first fiducial marker region connects to the first terminal portion of the main tubular body and a second portion of the bottom surface under the second fiducial marker region connects to the first terminal portion of the main tubular body;
   wherein the first fiducial marker region comprises a first code at a first portion of the top surface of the code platform;
   wherein the second fiducial marker region comprises a second code at a second portion of the top surface of the code platform;
   the first and the second fiducial marker regions both angled away from the main tubular body due to an angle of less than 180 degrees existing between the first portion of the top surface with the first fiducial marker region and the second portion of the top surface with the second fiducial marker region; and
   the code platform attached at the terminus of the first terminal portion.

12. A physical instrument comprising:
   a main tubular body with a first terminal portion and a second terminal portion, the second terminal portion comprising a tip;
   a code platform comprising a physical V formation, the code platform situated proximate to the first terminal portion of the main tubular body, the code platform including; a plurality of different codes; and
   a passage internal to the main tubular body, the passage extending through the first terminal portion and the tip at the second terminal portion;
   wherein the physical instrument comprises a sheath instrument;
   wherein an arm extends perpendicular from the main tubular body;
   wherein a first terminus of the arm is attached to the main tubular body and is proximate to the first terminal portion of the main tubular body; and
   wherein a second terminus of the arm is attached to the code platform;
   wherein the code platform comprises a top surface with a first fiducial marker region at a first portion of the top surface and a second fiducial marker region at a second portion of the top surface;
   wherein an angle of less than 180 degrees exists between an exposed first portion of a bottom surface of the code platform situated below first fiducial marker region and an exposed second portion of the bottom surface situated below the second fiducial marker region, wherein a portion of the arm connects to a portion of an intermediary panel situated between the first and the second portions of the top surface.

13. The physical instrument of claim 12, wherein the second surface of the code platform is closer to the second terminal portion of the main tubular body than the first surface of the code platform.

14. The physical instrument of claim 12, further comprising:
   wherein a first edge of the intermediary panel touches a portion of a first fiducial marker of the first fiducial marker region;
   wherein a second edge of the intermediary panel touches a portion of a second fiducial marker of the second fiducial marker region.

* * * * *